(12) United States Patent
Houde

(10) Patent No.: US 9,809,435 B2
(45) Date of Patent: Nov. 7, 2017

(54) COOLED PULSED LIGHT TREATMENT DEVICE

(75) Inventor: Eric Houde, Peyrolles en Provence (FR)

(73) Assignee: CLARANOR, Montfavet (FR)

( * ) Notice: Subject to any disclaimer, the term of this patent is extended or adjusted under 35 U.S.C. 154(b) by 0 days.

(21) Appl. No.: 13/504,090

(22) PCT Filed: Oct. 26, 2010

(86) PCT No.: PCT/FR2010/052291
§ 371 (c)(1),
(2), (4) Date: Jul. 9, 2012

(87) PCT Pub. No.: WO2011/051615
PCT Pub. Date: May 5, 2011

(65) Prior Publication Data
US 2012/0273693 A1    Nov. 1, 2012

(30) Foreign Application Priority Data

Oct. 30, 2009    (FR) ...................................... 09 57679

(51) Int. Cl.
*B67B 3/00* (2006.01)
*A61L 2/10* (2006.01)
(Continued)

(52) U.S. Cl.
CPC ................ *B67B 3/003* (2013.01); *A61L 2/10* (2013.01); *B65B 55/08* (2013.01);
(Continued)

(58) Field of Classification Search
CPC ............ A61L 2/10; B65B 55/08; B67B 3/003
(Continued)

(56) References Cited

U.S. PATENT DOCUMENTS 3,905,317 A * 9/1975 Pacilio ...................... A61L 2/24
192/125 A
4,910,942 A    3/1990 Dunn et al.
(Continued)

FOREIGN PATENT DOCUMENTS

DE    102004050493 A1 *    4/2006
EP          759529 A2 *    2/1997
(Continued)

*Primary Examiner* — Jason McCormack
*Assistant Examiner* — James Choi
(74) *Attorney, Agent, or Firm* — Greer, Burns & Crain, Ltd.

(57) ABSTRACT

A device and appliance is provided for the high-speed decontamination of objects by means of pulsed light, including: an illuminating structure suitable for illuminating a decontamination area in which the objects are arranged, the illuminating structure being suitable for producing streams of light pulses having wavelengths of 200 nm to 300 nm and an adjustable pulse rate; and a positioner suitable for positioning the objects in the decontamination area according to a predetermined arrangement, also including a cooler suitable for maintaining the temperature of the decontamination area substantially below a predetermined temperature when the decontamination area is illuminated, the cooler including an apparatus for circulating a cooling fluid built into the positioner.

15 Claims, 2 Drawing Sheets

(51) Int. Cl.
*B65B 55/08* (2006.01)
*B65B 7/28* (2006.01)

(52) U.S. Cl.
CPC ........ *A61L 2202/11* (2013.01); *A61L 2202/23* (2013.01); *B65B 7/2807* (2013.01)

(58) Field of Classification Search
USPC .................. 250/11; 198/836.1; 193/35 C
See application file for complete search history.

(56) References Cited

U.S. PATENT DOCUMENTS

| | | | |
|---|---|---|---|
| 5,003,185 A * | 3/1991 | Burgio, Jr. ................ 250/504 R |
| 6,054,097 A | 4/2000 | Mass et al. |
| 6,730,923 B1 * | 5/2004 | May et al. ................. 250/494.1 |
| 6,843,564 B2 * | 1/2005 | Putilin et al. ..................... 353/7 |
| 7,205,444 B1 * | 4/2007 | Chiu et al. ..................... 570/178 |
| 7,763,869 B2 * | 7/2010 | Matsushita et al. ...... 250/504 R |
| 2003/0147770 A1 * | 8/2003 | Brown et al. .................... 422/24 |
| 2006/0228251 A1 | 10/2006 | Schneberger et al. |
| 2008/0087523 A1 * | 4/2008 | Feierabend et al. .......... 198/409 |
| 2009/0045350 A1 * | 2/2009 | Humele ................. A61L 2/087 250/455.11 |
| 2009/0229795 A1 * | 9/2009 | Takatomi ............ B29C 49/6427 165/120 |
| 2011/0057115 A1 * | 3/2011 | Ferraguti ................ B67B 3/003 250/455.11 |
| 2012/0134878 A1 * | 5/2012 | Silvestri .......................... 422/22 |
| 2014/0138210 A1 * | 5/2014 | Buchhauser ....... B65G 47/5113 198/347.1 |
| 2016/0101201 A1 * | 4/2016 | Franc ....................... A61L 2/10 422/24 |

FOREIGN PATENT DOCUMENTS

| | | |
|---|---|---|
| WO | 00/38740 | 7/2000 |
| WO | 02/26270 | 4/2002 |
| WO | WO 2010128532 A1 * | 11/2010 |

* cited by examiner

COOLED PULSED LIGHT TREATMENT DEVICE

TECHNICAL FIELD

The present invention relates to a cooled pulsed light treatment device. It also relates to an appliance including such a device.

The field of the invention is more particularly but in a non-limiting way that of packaging and wrapping food and medical products.

BACKGROUND

The principle of decontamination and of sterilization through exposure to ultraviolet light pulses or flashes has long been known.

This technique makes use of the bactericidal efficiency of ultraviolet rays contained in intense white light flashes.

The decontaminating efficiency of pulsed light has been demonstrated on a wide range of micro-organisms: bacteria, molds, viruses, etc. The portion of UV radiation (between 200 and 300 nm) included in the flash results in, by the combination of a photothermal effect and a photochemical reaction, the destruction of micro-organisms present on the product subjected to the treatment.

The photochemical effect results from the absorption of UV rays by micro-organisms DNA. This absorption has maxima of about 200 nm and 247 nm, respectively. It causes disruptions and the formation of abnormal bonds within strands of DNA molecules, which prevent the replication thereof.

The photothermal effect is due to the fact that radiations absorbed by micro-organisms cause an abrupt increase in temperature. The absorption of received energy causes the disruption of cell membranes and the destruction of micro-organisms. The duration of this peak temperature, being a function of the duration of the light pulse, can be extremely short, typically in the order of a few hundred microseconds. The temperature rise (up to 150° C.) occurs at the microscopic level, whereas the temperature of the treated product does not substantially increase at the macroscopic level.

According to numerous works such as those of Wuytack et al. (Wuytack, E. Y., Thi Phuong, L. D., Aertsen, A., Reyns, K. M. F., Marquenie, D., De Ketelaere, B., et al., "Comparison of sublethal injury induced in *Salmonella enterica* serovar *Typhimurium* by heat and by different non thermal treatments", Journal of Food Protection, 2003, vol. 66, pp. 1071-1073), the association of two effects, that is photochemical and photothermal effect, would explain the efficiency of the pulsed light treatment.

Usually, light pulses are generated by means of xenon flash lamps. Flash lamps are arc lamps operating in a pulsed mode. The electrical energy is accumulated in an electrical capacitor. A high voltage (several tens kV) signal triggers arcing in the gas contained in the lamp. The released of electrical energy in turn produces a light emission through gas ionization. Xenon is the most efficient inert gas for converting electrical energy into light energy, in particular in the UV range. For gas pressures used (equal to or higher than 1 bar), the spectrum of flashes is continuous. It consists of wavelengths from UV to near infrared (200 to 1100 nm). The duration of these flashes is typically in the order of one hundred microseconds or more.

The decontamination level obtained is dependent on the number and the power of applied flashes, the nature of the treated surface, and ranges from the mere logarithmic reduction (destruction of a fraction of micro-organisms) to the full sterilization (almost complete destruction of micro-organisms).

U.S. Pat. No. 4,910,942 to Dunn et al. is known, wherein the authors give details about conditions for implementing the decontamination technique by pulsed light flashes for applications in the food processing and pharmaceutical industry: food packages, drug packages, plastic films, liquids, food (fish, cheese, cakes). The authors also give details about the decontaminating effect obtained in different cases as a function of the number of flashes and the energy (in joules) per flash.

The decontamination technique by pulsed light flashes is an athermal process at the macroscopic level, in that the implemented physical mechanisms (photochemical and photothermal effects) are macroscopically essentially athermal, and therefore do not cause on their own a substantial rise in the average temperature of the decontaminating objects. This property is important for the treatment of heat sensitive objects, and in particular for preserving organoleptic properties of food.

However, when implementing a decontamination technique by pulsed light flashes, the warming generally turns out to be an important problem which causes annoying limitations. This warming comes from the light energy absorption by objects to be decontaminated, but also and above all by the machine parts exposed permanently to the radiation and which contact these treated objects. The thermal effect of the radiation is all the more high as the xenon flash lamps used for practical and economical reasons emit more than 85% of their energy spectral density in the visible and infrared part of the light spectrum.

The thermal effects are generally limited in prior art devices on the one hand by limiting the illuminating rates, and thus the object treatment rates, and on the other hand by using lamps with excitation energy levels which enable the spectral part of UV radiation to be optimized, however at the expense of a high reduction in their lifetime.

The purpose of the present invention is to provide a cooled pulsed light treatment device, which allows high treatment rates compatible with needs for a use in a production line, of heat sensitive objects, while optimizing the operating costs.

SUMMARY

This object is achieved with a device for the high-speed decontamination of objects by means of pulsed light, including:
  an illuminating means for illuminating a decontamination area in which the objects are arranged, which illuminating means is suitable for producing streams of light pulses having wavelengths of 200 nm to 300 nm according to an adjustable pulse rate,
  a positioning means suitable for positioning the objects into the decontamination area according to a predetermined arrangement,
  a transfer means suitable for scrolling the objects in the decontamination area according to an adjustable scrolling rate, the pulse rate being adjusted such that each object receives in said decontamination area a predetermined number of light pulses,
  characterised in that it further includes a cooling means for maintaining the temperature of the decontamination area below a predetermined temperature when said decontamination area is illuminated, which cooling means includes a first means for circulating a cooling fluid built into the positioning means.

The positioning means can be arranged so that:
they include a throat shaped substantially to conform to the objects to be decontaminated, for slideably guiding them, and
at least one part of the walls of said throat thermally contacts at least one part of the walls of the first means for circulating the cooling fluid.

The illumination means can include:
a light source including a flash lamp, which flash lamp can contain for example xenon,
a metal reflector provided with a surface suitable for concentrating through reflection the light from said light source into the decontamination area.

Advantageously, the cooling means can further include:
a means for circulating a cooling fluid built into the reflector,
a means for circulating a cooling fluid arranged about the flash lamp, which means can include a quartz tube.

The means for circulating the cooling fluid can advantageously be fed by the same cooling fluid circuit, that is consisting of parts of a single circuit arranged in parallel and/or series.

The cooling fluid can advantageously include deionised water.

According to further advantageous characteristics,
the device according to the invention can further include a substantially transparent window in at least one part of the spectrum of the emitted light, which window is arranged on the light path between the reflector surface on the one hand, and the decontamination area on the other hand,
the transparent window can be of quartz,
the substantially transparent window can be attached to the reflector,
the cooling means can further include an air injecting means for circulating pressurized air in a space bounded by the reflector and the inner face of said transparent window,
the lamp, reflector, positioning means and decontamination area can extend substantially along a scrolling direction, and the means for circulating the cooling fluid can include substantially rectilinear tubes, arranged substantially along said scrolling direction,
the cooling means, in particular the tubes, can consist of materials not altering deionised water, such as SS (or stainless steel).

According to one embodiment, the device according to the invention can advantageously further include at least one substantially scattering retroreflector, arranged along at least one of the walls of the decontamination area. This (these) retroreflector(s) can for example be used to illuminate under better conditions some areas when the objects are suitable thereto. Mention can be made in particular of the case of objects provided with several openings, in which case it becomes possible to eliminate outer areas of the objects at the periphery of these openings. The retroreflectors can be made for example by bonding a retroreflecting support, applying paint, or treatment (polishing, . . . ) of the wall of the decontamination area.

According to an advantageous embodiment of the invention wherein the implemented lamp is a xenon flash lamp, the control circuit of the lamp can be configured such that the electrical energy injected into the lamp at each pulse is determined such that the life expectancy of the lamp is higher than ten million pulses.

This amounts to limiting the electrical energy injected into the lamp to increase the lifetime thereof. Of course, this limitation is only performed when a light intensity has to be maintained in the UV-C range compatible with the decontamination needs. This operating mode enables the maintenance costs of the decontamination system to be decreased to a high rate, but it is thermally detrimental. It is made possible in the device according to the invention by the implemented cooling means.

Indeed, the spectrum of such a xenon flash lamp ranges from infrared to ultraviolet. It is known that the ultraviolet part and more specifically the so-called UV-C range, that is wavelengths of 200 nm to 300 nm are essential to decontamination. However, it is now not possible to obtain xenon lamps having a good yield in the UV-C range without penalizing the lifetime thereof. Indeed, the lifetime (V) of a xenon arc lamp is related to the applied energy (E) by the following relationship:

$$V \sim E^{-8.5}.$$

For example, a lamp receiving 300 Joules in 200 µs and reemitting 150 Joules of which 10% are in the UV-C part of the spectrum has a lifetime in the order of 3 million flashes. By doubling the injected energy, the spectral proportion of the UV-C range changes to 14% but the lifetime of the lamp is brought down to 8000 flashes. That is why, under conditions of use allowing a reasonable lifetime, in the order of 90% of the spectrum emission of the lamp are in the visible or infrared part of the spectrum and only results in providing heat.

The present invention also relates to a pulsed light decontamination appliance integrating the device, characterised in that it is implemented in a production line.

Such an appliance can be implemented for example to decontaminate the following objects:
bottle caps,
bottle caps having a second opening opposite to the opening suitable for being attached to the bottle, commonly called "sport" caps,
bottle preforms, in particular of PET.

BRIEF DESCRIPTION OF THE DRAWINGS

Other advantages and features of the invention will appear upon reading the detailed description of implementations and embodiments in no way limiting, and the following appending drawings wherein.

DETAILED DESCRIPTION

Figure 1:
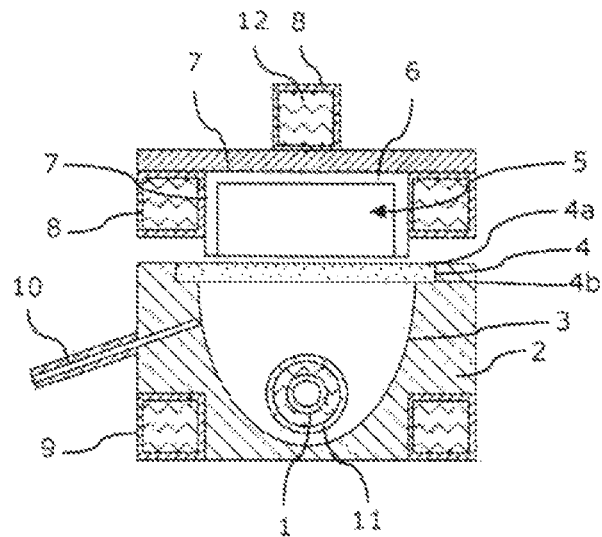
FIG. 1 illustrates a first embodiment of the device according to the invention, enabling bottle caps to be decontaminated.
Figure 3:
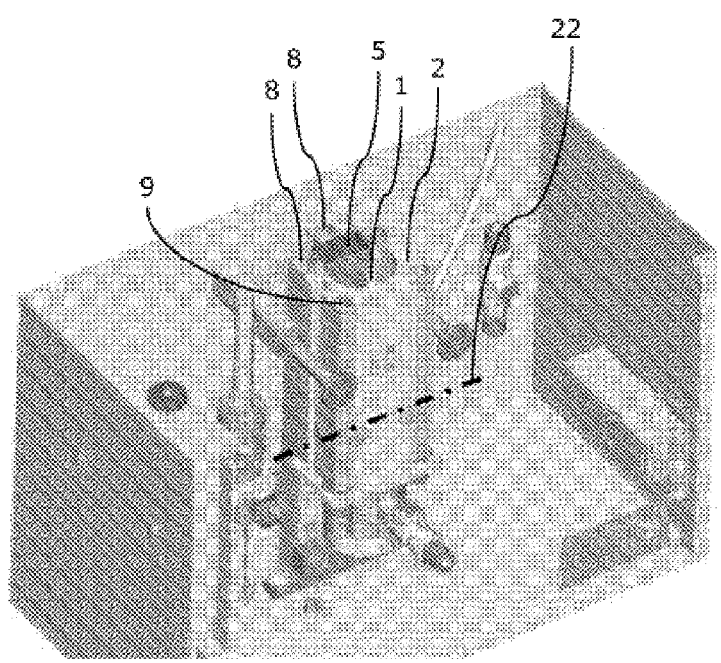

In reference to FIG. 1, the device according to the invention is advantageously implemented in an apparatus for decontaminating bottle caps for food industry. This appliance can in particular be set in a production line for decontaminating caps before filling and closing the bottles. The caps are for example of PE (polyethylene) or PP (polypropylene) and the bottles are of PET (polyethylene terephthalate). A perspective view of the same device is shown in FIG. 3. FIG. 1 corresponds to a cross-section view of the device along the axis 22.

The device includes an optical cavity consisting of a reflector 2 closed by a transparent window 4 preferably of quartz, and a xenon flash lamp 1 having a tubular shape. The lamp 1 is itself inserted inside a quartz tube 11 wherein the cooling liquid 12 circulates, which is preferably, but in no way limiting, deionised water. The reflector 2 is preferably of polished aluminum and it is cooled by substantially square cross-section tubes 9 preferably of stainless steel plated on the body of the reflector 2 and wherein the cooling liquid also circulates.

The shape of the surface 3 of the reflector 2 is calculated to optimally illuminate the decontamination area 5. Facing the cavity are guides 7 for circulating objects to be decontaminated 6, such as caps. These guides 7 make up a throat shaped substantially to conform to the objects 6. They are adjoining to substantially square cross-section tubes 8 preferably of stainless steel also cooled by a circulation of the cooling liquid. Advantageously, at least one part of the cooling tubes 8 is directly used to guide the objects 6, so as to optimize heat exchanges. The window 4 also takes part in guiding the objects 6.

A bottle packaging line can operate to a rate in the order of 72,000 bottles per hour. The device according to the invention, when inserted into this line, could thus be able to treat 20 caps per second. In a device such as the one shown in FIG. 3, the decontamination area 5 has a length such that four caps can be simultaneously treated. The light pulse emission rate necessary for each cap to receive at least one flash is thus 5 Hz to the minimum, for a decontamination of 3 logs (that is a reduction by a factor 1,000 of the number of micro-organisms present after treatment).

Lamps usually used to treat caps emit a high average optical power, for example in the order of 750 W for pulses of 150 Joules emitted at 5 Hz. The warming of caps 6 remains mild because they only receive one or two flashes. Besides, different pieces of the machine such as the guides 7 and reflectors 2, which are motionless, permanently receive this power and are susceptible to be strongly warmed. Depending on their very nature, for example aluminum or stainless steel, these pieces can absorb between 10 and 40% of the incident radiation. Accordingly, if no particular caution is taken, when the caps 6 of plastic material contact these very hot pieces, at 100° C. or more, they might be molten or even to be ignited. This can result in the caps being blocked, the production stopped and the machine damaged. Thus, the cooling means such as the tubes 8 integrated to the guiding elements 7, which are an object of the present invention, make up elements essential to implement the device given that they enable the heat of the static parts to be removed from the decontamination area 5, such that surfaces surrounding the objects 6 do not exceed a maximum temperature, for example 100° C.

Furthermore, the warming of the reflector 2 should be avoided because the caps 6 circulate in contact with the window 4 which closes the optical cavity. If this cavity is warmed, this increases the temperature of the window 4, which can also cause the caps to melt. The temperature control of this window 4 is advantageously provided in the device according to the invention by the cooling means such that the tubes 9 in the reflector 2 and the tube 11 about the lamp 1.

When the power dissipated in the device is high, for example when two lamps operating at 5 Hz and dissipating a total power of 1,500 W are implemented, the window 4 can also advantageously be cooled by injecting filtered air 10 on its face 4b located on the lamp 1 side.

Figure 2:
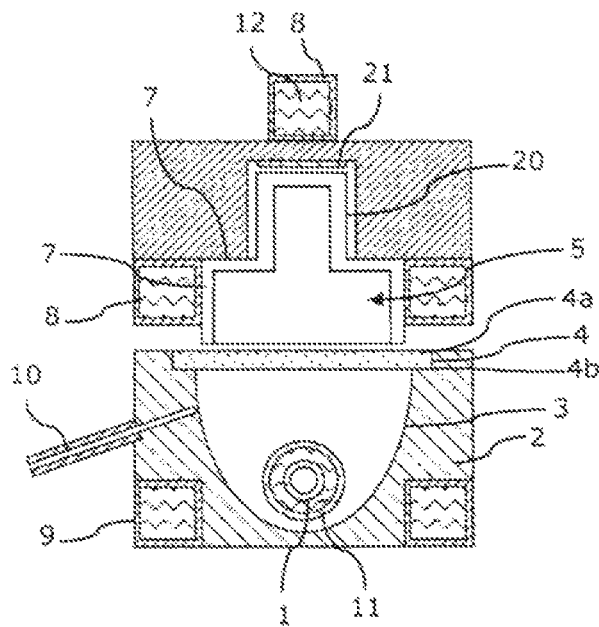
FIG. 2 illustrates a second embodiment of the device according to the invention, enabling "sport" bottle caps to be decontaminated, FIG. 3 gives a view of an appliance according to the invention.

In reference to FIG. 2, according to a second embodiment, when the objects 20 are partially transparent or have openings, one or more backscatters 21 can be arranged on the guides 7 so as to backscatter light onto the faces which are not directly illuminated. In particular, a device according to the invention advantageously enables "sport" bottle caps 20 to be decontaminated, which caps are provided with a second opening opposite to the part which is attached to the bottle, allowing to drink without unscrewing them. The retroreflector 21 as shown in FIG. 2 is illuminated through this second opening and sends back light so as to illuminate and decontaminate the outer rims of the cap 20 about this second opening.

According to particular embodiments:
all the elements wherein the cooling liquid circulates can be connected to the same circuit;
in a device having an essentially elongated shape as shown in FIG. 3, the cooling means 8, 9, 11 can be arranged in parallel with respect to the liquid circulation;
it is possible to use any type of cooling liquid without departing from the scope of the invention;
the source 1 can include any type of sources compatible with the application. In particular, it can be an excimer lamp or a laser;
the window 4 can have a treatment, or include a material such that it allows only part of the optical spectrum of the source 1 to pass. In particular, the window 4 can be a dichroic blade blocking the infrared radiation which is the cause of the major part of the thermal effect.

A device according to the invention can of course be implemented for decontaminating any type of objects, from which there can be mentioned by way of non-limiting examples lids and pots. A device according to the invention can also be advantageously implemented for decontaminating objects having a dimension greater than the decontamination area and scrolling therein on substantially motionless supports, such as for example films of plastics or consisting of other materials.

Of course, the invention is not limited to the examples just described and numerous alterations can be provided to these examples without departing from the scope of the invention.

The invention claimed is:

1. A device for the high-speed decontamination of solid objects to be decontaminated by means of pulsed light, the device being designed for decontaminating objects including bottle caps, bottle preforms, lids, pots or films, the device comprising:
an illuminating means including an optical cavity for illuminating a decontamination area in which the objects are arranged, wherein said illuminating means is configured to produce streams of light pulses having wavelengths of 200 nm to 300 nm according to an adjustable pulse rate;
a positioning means suitable for positioning the objects in the decontamination area according to a predetermined arrangement, said positioning means comprising motionless guides facing said optical cavity, said guides forming at least part of a throat-shaped space in said decontamination area that conforms to a shape of the objects to be decontaminated including bottle caps, bottle performs, lids, pots or films, said guides directly contacting at least two sides of each of the objects to independently and sequentially guide each of the objects through said throat-shaped space and in front of the illuminating means such that no object to be decontaminated is obstructed by another object to be decontaminated; and a transfer means suitable for scrolling the objects in the decontamination area according to an adjustable scrolling rate, the pulse rate being adjusted such that each solid object receives a predetermined number of light pulses in said decontamination area; said guides each including a cooling fluid and forming cooling tubes, said cooling tubes configured to directly cool said at least two sides of each of the objects in said decontamination area and maintain a temperature of said decontamination area below a predetermined temperature when said decontamination area is illuminated.

2. The device according to claim 1, wherein the illuminating means includes:

a light source comprising a flash lamp, a metal reflector provided with a surface suitable for concentrating through reflection the light from said light source into the decontamination area.

3. The device according to claim 2, further comprising cooling means configured to circulate a cooling fluid built into the reflector.

4. The device according to claim 2, further comprising cooling means configured for circulating a cooling fluid arranged about the flash lamp.

5. The device according to claim 1, wherein the cooling tubes are fed by a cooling fluid circuit.

6. The device according to claim 1, wherein the cooling fluid includes deionized water.

7. The device according to claim 2, further comprising a substantially transparent window in at least one part of the spectrum of the emitted light, wherein said transparent window is arranged on the light path between the surface of the reflector and the decontamination area and takes part in guiding the objects.

8. The device according to claim 7, further comprising cooling means, wherein said transparent window is attached to the reflector such that the cooling means further includes an air injecting means for circulating pressurized air into a space bounded by the reflector and the inner face of said transparent window.

9. The device according to claim 2, wherein the lamp, the reflector, the positioning means and the decontamination area substantially extend along a scrolling direction, and the cooling tubes are substantially rectilinear tubes, substantially arranged along said scrolling direction.

10. The device according to claim 1, further comprising at least one substantially scattering retroreflector, arranged along at least one wall of the decontamination area.

11. The device according to claim 2, wherein the electrical energy injected into the lamp at each pulse is determined such that the life expectancy of the lamp is higher than ten million pulses.

12. A pulsed light decontamination appliance including the device according to claim 1, wherein the appliance is suitable for being implemented in a production line.

13. The pulsed light decontamination appliance according to claim 12, wherein the decontaminated objects are bottle caps.

14. The pulsed light decontamination appliance according to claim 12, wherein the decontaminated objects are "sport" bottle caps which have a second opening opposite to the opening suitable for being attached to the bottle.

15. The pulsed light decontamination appliance according to claim 12, wherein the decontaminated objects are bottle preforms.

* * * * *